US005277897A

United States Patent [19]

Piwnica-Worms et al.

[11] Patent Number: 5,277,897
[45] Date of Patent: Jan. 11, 1994

[54] IN VIVO ENHANCEMENT OF CELLULAR ACCUMULATION OF LIPOPHILIC CATIONIC ORGANOMETALLIC COMPOUNDS BY REDUCTION OF INTRAMEMBRANE POTENTIAL

[75] Inventors: David R. Piwnica-Worms, Wellesley; James F. Kronauge, Brookline, both of Mass.

[73] Assignee: Brigham and Women's Hospital, Boston, Mass.

[21] Appl. No.: 945,916

[22] Filed: Sep. 17, 1992

Related U.S. Application Data

[62] Division of Ser. No. 594,813, Oct. 10, 1990, Pat. No. 5,186,923.

[51] Int. Cl.$^5$ ............... A61K 49/00; A61K 31/28; A61K 31/69
[52] U.S. Cl. ................................ 424/1.65; 424/4; 424/7.1; 424/9; 514/64; 514/836; 514/946; 514/492
[58] Field of Search .............. 424/1.1, 4, 9, 7.1; 514/64, 836, 946, 492

[56] References Cited

U.S. PATENT DOCUMENTS 3,873,296 3/1975 Ashmead et al. ............... 71/77
4,946,683 8/1990 Forssen ............................ 424/422

OTHER PUBLICATIONS

Piwnica-Worms, David et al., "Editorial: Noncardiac Applications of Hexakis-(alkylisonitrile) Technetium-99m Complexes", *J. Nucl. Med.* 31(7):1166-1167 (1990).

Piwnica-Worms, David et al., "Enhancement of Hexakis(methoxyisobutylisonitrile)$^{99m}$Tc (Tc-MIBI) Accumulation in Cultured Chick Embryo Myocardial Cells by Tetraphenylborate", *Circulation* 82(4):Suppl. III, No. 1931 (1990).

Ramsay, Rona R. et al., "Enhancement by Tetraphenylboron of the Interaction of the 1-Methyl-4-Phenylpyridinium Ion (MPP+) with Mitochondria", *Biochem. Biophys. Res. Comm.* 159(3):983-990 (1989).

Meerdink, Denis J. et al., "Comparison of Hypoxia and Ouabain Effects on the Myocardial Uptake Kinetics of Technetium-99m Hexakis 2-Methoxyisobutyl Isonitrile and Thallium-201", *J. Nucl. Med.* 30:1500-1506 (1989).

Melnik, Eugene et al., "Phloretin-Induced Changes in Ion Transport across Lipid Bilayer Membranes", *J. Gen. Physiol.* 69:243-257 (1977).

Neef, Cees et al., "Hepatic Uptake and Biliary Excretion of Organic Cations-II: The Influence of Ion Pair Formation", *Biochem. Pharmacol.* 33(24):3991-4002 (1984).

Chiu, Mary L. et al., "Effect of Mitochondrial and Plasma Membrane Potentials on Accumulation of Hexakis (2-Methoxyisobutylisonitrile)Technetium(I) in Cultured Mouse Fibroblasts", *J. Nucl. Med.* 31:1646-1653 (1990).

Chiu, Mary L. et al., "Monitoring Mitochondrial and Plasma Membrane Potentials in Cultured Cells with a (List continued on next page.)

Primary Examiner—Glennon H. Hollrah
Assistant Examiner—Gary C. Hollinden
Attorney, Agent, or Firm—Sterne, Kessler, Goldstein & Fox

[57] ABSTRACT

The invention relates to compositions that comprise (1) lipophilic cationic organometallic complexes, particularly hexakis(2-methoxyisobutylisonitrile)technetium(I) complex, and (2) an agent that decreases the intramembrane potential of a living cell. Agents which decrease the intramembrane potential of a living cell include the lipophilic anions, especially tetraphenylborate anion. The invention also relates to methods in which the compositions are administered in vivo and in vitro when it is desirable to obtain enhanced cellular accumulation of lipophilic cationic organometallic complexes. The compositions and methods are useful for diagnosis and treatment, particularly in vivo tissue imaging.

16 Claims, 12 Drawing Sheets

OTHER PUBLICATIONS

New $^{99m}$Tc-based Lipophilic Cation", *J. Gen. Physiol.* 94:41a (1989).

Flewelling, Ross F. et al., "Hydrophobic Ion Interactions with Membranes: Thermodynamic Analysis of Tetraphenylphosphonium Binding to Vesicles", *Biophys. J.* 49:531–540 (1986).

Sinusas, A. J. et al., "Correlation of Myocardial Uptake of Technetium-99m Methoxy-Isobutyl Isonitrile with Regional Flow during Coronary Occlusion and Reperfusion", *J. Nucl. Med.* 30:756 [Entry No. 115] (1989).

Altendorf, Karlheinz et al., "Accumulation of Lipid-Soluble Ions and of Rubidium as Indicators of the Electrical Potential in Membrane Vesicles of *Escherichia coli*", *J. Biol. Chem.* 250(4):1405–1412 (1975).

Bakeeva, L. E. et al., "Conversion of Biomembrane—Produced Energy into Electric Form", *Biochim. et Biophys. Acta* 216:13–21 (1970).

Cheng, Kang et al., "Measurement of Membrane Potentials ($\psi$) of Erthrocytes and White Adipocytes by the Accumulation of Triphenylmethylphosphonium Cation", *J. Membrane Biol.* 56:191–201 (1980).

IN VIVO ENHANCEMENT OF CELLULAR ACCUMULATION OF LIPOPHILIC CATIONIC ORGANOMETALLIC COMPOUNDS BY REDUCTION OF INTRAMEMBRANE POTENTIAL

STATEMENT AS TO RIGHTS TO INVENTIONS MADE UNDER FEDERALLY-SPONSORED RESEARCH AND DEVELOPMENT

Part of the work performed during development of this invention utilized U.S. Government funds. The U.S. Government has certain rights in this invention.

This application is a division of application Ser. No. 07/594,813, filed Oct. 10, 1990. U.S. Pat. No. 5,186,923.

BACKGROUND OF THE INVENTION

1. Field of the Invention

The present invention relates to compositions comprising a lipophilic cationic organometallic complex and an agent that decreases the intramembrane potential in a cell and methods whereby these compositions may be used in vitro and in vivo. The reduction in intramembrane potential results in enhancing the cellular accumulation of the lipophilic cationic organometallic compounds.

2. Description of the Background Art

Hexakis (alkylisonitrile) technetium (I) complexes are a class of low valence technetium ($^{99m}$Tc) coordination compounds empirically designed as clinical myocardial perfusion imaging agents (Jones, A. G. et al. *Int. J. Nucl. Med. Biol.* 11:225-234 (1984), Holman, B. L., et al., *J. Nucl. Med.* 25:1350-1355 (1984), Holman, B. L., et al., ibid 28:13-18 (1987), Sporn, V., *Clin. Nucl. Med.* 13:77-81 (1988)). Conceived to be used in a manner similar to thallous chloride for the noninvasive evaluation of coronary artery disease, the compounds exploit the more favorable emission characteristics of $^{99m}$Tc for applications in clinical imaging (Strauss, H. W., et al., *Radiology* 160:577-584(1986), Deutsch, E., et al., *Science* 214:85-86(1981)). Chemical analysis of these complexes with the ground state $^{99}$Tc isotope shows them to be monovalent cations with a central Tc(I) core octahedrally surrounded by six identical ligands coordinated through the isonitrile carbon. The terminal alkyl groups, when bound to the technetium, encase the metal with a sphere of lipophilicity (Jones, A. G., et al., *Int. J. Nuc. Med. Biol.* 11:225-234 (1984), Mousa, S. A., et al., *J. Nuc. Med.* 28:1351-1357 (1987)).

While the complex has proven highly successful as a clinical flow tracer (Holman, B. L., et al., *J. Nucl. Med.* 25:1350-1355 (1984); Wacker, F. J., et al., *J. Nucl. Med.* 30:301-311 (1989)), evidence has demonstrated a component of myocardial localization dependent on tissue viability (Piwnica-Worms, D., et al., *J. Nucl. Med.* 31:464-472 (1990); Rocco, T. P., et al., *J. Am. Col. Card.* 14:1678-1684 (1989); Sinusas, A. J., et al., *J. Nucl. Med.* 30:756 (1989)).

In the course of investigating mechanisms of cellular retention of these agents, studies demonstrated that neither the lipophilic properties nor the cationic charge alone were sufficient to characterize the uptake properties of these complexes (Piwnica-Worms, D., et al., *Invest. Radiol.* 24:25-29 (1989)). The requirement of lipophilicity and cationic charge for myocardial localization raised the possibility that their cellular uptake and retention mechanisms are in part determined by mitochondrial and plasma membrane potentials in a manner analogous to several other known permeant cationic probes of membrane potential (Deutsch, C. J., et al., *J. Cell. Phys.* 99:79-93 (1979); Litchtshtein, D., et al., *Proc. Nat'l. Acad. Sci. U.S.A.* 76:650-654 (1979); Bussolati, O., et al., *Biochim. et Biophys. Acta* 854:240-250 (1986); Akerman, K. E., et al., ibid 546:341-347 (1979); Johnson, L. V., et al., *Proc. Nat'l. Acad. Sci. U.S.A.* 77:990-994 (1980); Johnson, L. V., et al., *J. Cell. Biol.* 88:526-535 (1981); Davis, S., et al., *J. Biol. Chem.* 260:13844-13850 (1985)).

Subsequent studies of cellular uptake of hexakis(methoxyisobutylisonitrile) technetium, a member of the isonitrile class of coordination compounds, suggested that the uptake of the compound was affected by alterations in the plasma and mitochondrial membrane potentials (Delmon-Moingeon, L. I. et al., *Cancer Res.* 50:2198 (1990); Chiu, M. L., et al., *J. Nucl. Med.:* 31:1646-1653 (1990)).

Data from whole organ cardiac preparations also provide indirect evidence for this model of cellular uptake. In perfused rabbit heart, oaubain ($1.5 \times 10^{-6}$M) and hypoxia alter net tissue extraction of Tc-MIBI (Meerdink, D. J., et al., *J. Nucl. Med.* 30:1500-1506 (1989)). In perfused rat hearts, metabolic inhibition with sodium cyanide (10 mM) blocks 50% of Tc-MIBI accumulation while membrane disruption with Triton X100 (0.5%) inhibits 86% of net uptake (Beanlands, R., et al., *Circ.* 80(S II):545 (1989)). In sum, the data are consistent with a membrane transport process for Tc-MIBI, like other non-metallic lipophilic cations, involving a non-carrier-mediated translocation and passive distribution of the agent in response to an imposed transmembrane potential.

Other uptake models for hexakis (alky isonitrile) technetium complexes have been proposed. Simple lipid partitioning was initially thought to be the sole mechanism of localization. In this context, lipophilicity was found to correlate well with cellular uptake studies and imaging intensity in vivo for the more lipophilic agents developed early in this class (Piwnica-Worms, D., et al., *Invest. Radiol.* 24:25-29 (1989)), although exceptions to the trend indicated other factors were involved. Alternatively, binding of Tc-MIBI (an agent of intermediate lipophilicity) to an 8-10 KDalton cytosolic protein has been proposed (Mousa, S. A., et al., *J. Nucl. Med.* 27:p995 (1986)).

In evaluating the relative merit of these models, a novel prediction of the potential-dependent uptake mechanism for Tc-MIBI is the augmentation of uptake kinetics by lipophilic anions. In human lymphocytes (Deutsch, C. J., et al., *J. Cell. Physiol.* 99:79-94 (1979)), for example, the kinetics of plasma membrane translocation of tetraphenylphosphonium (TPB), another well characterized permeant cationic probe of membrane potential, are augmented by the presence in the incubation buffer of the lipophilic anion tetraphenylborate (TPB). In addition, low concentrations of TPB increase uptake kinetics of other lipophilic cations into isolated heart mitochondria (Bakeeva, L. E., et al., *Biochim. Biophys. Acta* 216:13-21 (1970)), vesicles prepared from E. coli (Altendorf, K., et al., *J. Biol. Chem.* 250:1405-1412 (1975)), and isolated perfused rat liver (Neef, C., et al., *Biochemical Pharm.* 33:3991-4002 (1984)).

SUMMARY OF THE INVENTION

The present invention is based upon the inventors' unexpected discovery that a decrease in the intramembrane potential will result not only in an increase in the rate of uptake but also in an enhanced accumulation level of organometallic lipophilic cationic complexes in a cell in which the decrease in potential occurs.

Accordingly, the present invention includes compositions for enhancing the intracellular accumulation of lipophilic organometallic complexes.

The present inventors have designed compositions containing technetium complexes and agents that produce the decrease in intramembrane potential. The exemplified compositions contain a specific hexakis(alkylisonitrile)technetium(I) complex and an agent that reduces the intramembrane potential in a cell. These agents include, but are not limited to, lipophilic anions and dipolar compounds. Preferred embodiments are compositions in which the agent is tetraphenylborate ion, 8-anilino-1- naphthalene sulfonate ion, or phloretin. Although the preferred compositions may include all members of the hexakis(alkylisonitrile)technetium(I) class, a more preferred embodiment of the present invention comprises compositions containing hexakis(methoxyisobutylisonitrile)technetium(I) (Tc-MIBI).

The present invention also includes methods for enhancing the intracellular accumulation of lipophilic cationic organometallic complexes, such as hexakis (alkylisonitrile) technetium(I) complexes, by the coadministration of a complex and an agent that reduces the intramembrane potential of a cell. The cell may be in vivo or in vitro.

The methods of the present invention that are effective in vivo include, but are not restricted to, diagnostic methods in which the organometallic complex is formulated with a radioisotope suitable for detection as a diagnostic agent and methods of treatment in which the complex is comprised of a radioisotope or other component suitable for therapy.

Methods of the present invention also include in vivo and in vitro cell labelling. When performed in vivo, the imaging may be used to detect both abnormal and normal cells. In addition to cell labelling, the methods of the present invention can be used to image normal body tissue, such as whole organs, and abnormal body tissue such as tumors.

The methods of the present invention use compositions that comprise a combination of a lipophilic cationic organometallic complex and an agent that decreases the intramembrane potential. In a preferred embodiment, methods of the present invention are effected with a composition that contains a combination of Tc-MIBI and tetraphenylborate.

Following the administration of the compositions of the present invention, the complex is accumulated in living cells at levels well in excess of the levels of accumulation that are found when the complex is administered in the absence of the agent. This invention thus enhances the agent's potential usefulness as a diagnostic and therapeutic tool.

DESCRIPTION OF THE PREFERRED EMBODIMENTS

Figure 1:
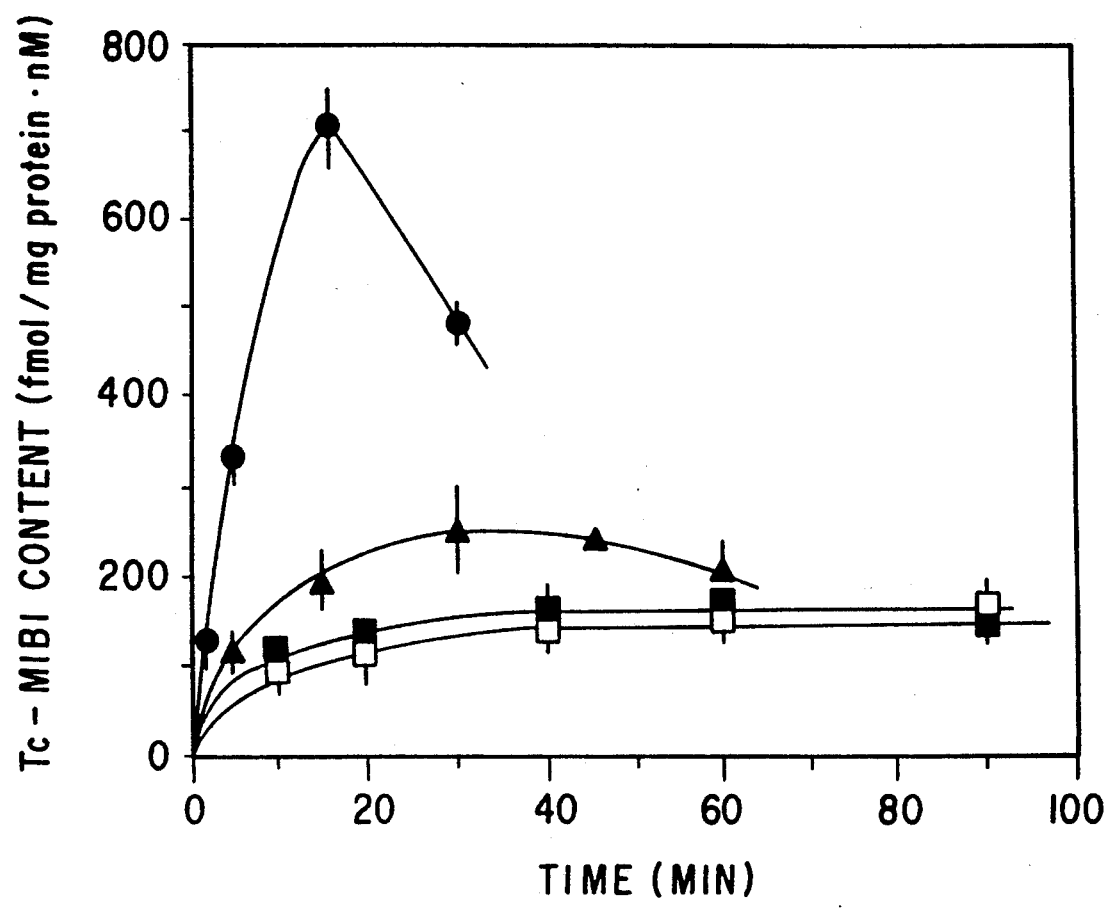
FIG. 1. Effect of TPB on net accumulation of Tc-MIBI in cultured chick heart cells. Preparations were incubated for the times indicated in Modified Earle's Basic Salt Solution (MEBSS) control buffer containing tracer Tc-MIBI alone (□) and with various concentrations of tetraphenylborate: (■) $10^{-9}$M; (▲) $5 \times 10^{-7}$M; (·) $10^{-5}$M. Results are expressed as fmol cellular Tc-MIBI/mg protein per nM extracellular Tc MIBI. Each point represents the mean ±SEM of 3 determinations.

The present invention relates to lipophilic cationic organometallic complexes, preferably compositions comprising hexakis(alkylisonitrile)technetium(I) complexes, and an agent that decreases the intramembrane potential of a cell and methods whereby these compositions may be used in vitro and in vivo.

In a more preferred embodiment of the present invention the composition comprises hexakis(methoxyisobutylisonitrile)technetium(I) (Tc-MIBI) and tetraphenylborate ion. Other preferred embodiments include compositions comprising Tc-MIBI and either phloretin (3-(4-hydroxyphenyl)-1-(2,4,6-trihydroxyphenyl)-1-propanone; 2',4',6'-trihydroxy-3-(p-hydroxyphenyl)-propriophenone) or 8-anilino-1 naphthalene sulfonic acid. Further embodiments of the present invention include compositions that are combinations of other hexakis(alkylisonitrile)technetium complexes and any agent that decreases the cellular intramembrane potential. Examples of such agents are lipophilic anions other than TPB, such as, 8-anilino-1-naphthalene sulfonic acid, phenyl dicarbaundecaborane and trinitophenol and dipolar compounds other than phloretin such as phloroacetophenone and p-nitrophenol. Other biologically compatible fluorescent dyes such as fluorescein derivatives may also be useful.

Tc-MIBI in particular, but not exclusively, in this class of compounds, possesses the unique combination of properties required to be a probe of biological membrane potential. This compound is sufficiently lipophilic to partition into and through the hydrophobic core of biological membranes, but also combines this property with a delocalized cationic charge which renders the compound responsive to the plasma and mitochondrial transmembrane potentials. This combination of lipophilicity and delocalized charge produces an unusual property for these pharmaceuticals. Unlike tissue binding of many other pharmaceuticals that depend on highly specific binding sites (high affinity receptors), these pharmaceuticals have a non-specific uptake mechanism. However, tissue interaction is highly specific for those tissues with high plasma membrane potentials, high mitochondrial membrane potentials, or high mitochondrial content, or combinations of the above.

A major obstacle of the use of these pharmaceuticals in patients has been the low extraction fraction on first pass (Leppo, J. A., et al., Circ. Res. 65:632-639 (1989). Because the uptake by tissues is time-dependent, any drug delivered via the blood to a tissue may not have enough time to be transported into the cells of the target organ (heart, for example) before being washed out of that vascular bed and onto other non-target tissues (liver, kidney, for example).

Physiological studies with myocellular preparations have recently indicated that the fundamental biophysical mechanism of uptake and retention of Tc-MIBI is both mitochondrial and plasma membrane potential-dependent (Piwnica-Worms, D., et al., Circ. (in press); Chiu, M. L., et al., J. Nucl. Med. 31:1646-1653 (1990)).

In cultured chick myocardial cells, for example, depolarizing either plasma membrane potentials with high potassium (K.) buffer or mitochondrial membrane potentials with the metabolic uncoupler carbonyl cyanide-m-chlorphenylhydrazone (CCCP) decreases the unidirectional influx and net cellular accumulation of TC-MIBI. Conversely, hyperpolarizing mitochondrial membrane potentials with the ionophore nigericin, a $K^+/H^+$ exchanger, increases net cellular uptake of Tc-MIBI. In addition, mitochondrial hyperpolarization by oligomycin-induced inhibition of proton influx through the $F_1F_0$-ATP synthase increases Tc-MIBI uptake or retention. However, sodium azide in combination with oligomycin virtually eliminates net uptake of the agent.

To further test a proposed model of Tc-MIBI myocellular accumulation and to provide insight into a rational approach for augmenting tissue extraction of Tc-MIBI in vivo, the response of myocellular transport of Tc-MIBI to permeant and impermeant anions as well as various K concentrations were evaluated in cultured chick embryo heart cells. It was reasoned that understanding the biophysical mechanism of subcellular localization may assist experiments into cellular metabolism and furthermore enable this agent to be applied to the whole organism and humans as a tracer of tissue energetics in vivo. Both uptake kinetics and net accumulation of Tc-MIBI were evaluated in the presence of agents that reduce membrane potential.

The present inventors have discovered that the addition of a compound that decreases the intramembrane potential not only increases the kinetics of uptake, as might be theoretically expected, but also dramatically increases net accumulation of the Tc-MIBI into cells and mitochondria. Suitable compounds include, but are not limited to, lipophilic anions, exemplified by tetraphenylborate, and dipolar compounds, exemplified by phloretin. Reduction of the potential within the membrane allows more easy passage of lipophilic cationic organometallic compounds such as Tc-MIBI into the target cells.

Thus, prior to the present invention, the advantageous properties of Tc complexes could not be fully advantageously exploited for broad clinical use.

As discussed above, an advantageous property of Tc-MIBI is that the uptake by tissues is non-specific. Thus, any living cell (and potentially, any tissue type) can retain the molecule. A further advantage is that Tc-MIBI has been shown to be safe in humans as a diagnostic pharmaceutical while maintaining the unique combination of properties that allow it to respond to membrane potential. Conversely, other classes of lipophilic cations or fluorescent probes of membrane potential (e.g., rhodamine 123) have been shown to be toxic to cells and mitochondria (Bernel, et al. Science 218:1117-1119 (1982), Emaus, R. K., et al. Biochim.

Biophys. Acta 850:436-448 (1986), Gear, A. R. L. *J.Biol. Chem.* 249:3628-3637 (I974)). These compounds have not been injected into humans.

One preferred embodiment relates to the source of the isotope. The specific activity of the Tc-MIBI complex synsthesized from TcO$_4^-$ obtained directly from commercial molybdenum/technetium generators, is extremely high. For example, in various embodiments disclosed herein, Tc-MIBI was generally synthesized at 1-6×10$^8$ Ci/mole. By comparison, [$^3$H] TPP+, another lipophilic cation, is commonly supplied commercially at 5-100 Ci/mole. This provides an opportunity to decrease the molar concentration of cation accumulation by the biological preparation, yet remain within detectable limits. Since rhodamine 123 and TPP+ have been reported to have toxic effects on mitochondrial function at typical loading activities, the high specific activity and therefore low concentrations of Tc-MIBI required for biological experiments minimize toxic side effects during physiological experimentation and clinical imaging with the enhancement process.

Accordingly, a preferred embodiment of the present invention is the use of Tc-MIBI for myocardial perfusion imaging, in humans or veterinary animals, by co-administration of Tc-complexes and agents that decrease the intramembrane potential. The co-administration enhances accumulation of the drug in the target tissue such that the tissue can be more effectively imaged in vivo.

In alternative embodiments, the compositions can be used to image tissues other than heart. Examples of tissues that could be imaged are the organs normally found in the body and abnormal body tissues such as tumors. Other organs and functions that could be imaged with the compositions include hepatobiliary function and excretion, metastatic tumor deposits in the liver, pulmonary perfusion and pulmonary thromboembolic disease, renal perfusion and excretory function, skeletal muscle perfusion and abnormalities of both skeletal muscle and myocardial energetics as may occur in cardiomyopathies and diseases of mitochondrial dysfunction such as mitochondrial cytopathies or "ragged red fiber" disease. This composition could also be used for functional tests of cellular or tissue energetics in vitro as, for example, in a test of cellular integrity of lymphocytes after Indium-IU labelling.

In another embodiment, the compositions of the present invention may be used to treat disease by the enhancement of tissue uptake of therapeutic pharmaceuticals. For example, tumor therapy using cytotoxic agents directed at tumor mitochondria could be enhanced as could the cellular toxicity of chemotherapeutic agents. Along this line, enhanced tumor uptake of radiation sensitizing agents could be promoted. Toward these ends we disclose embodiments exemplary of the uptake and retention of Tc complexes in the presence of such agents.

In an alternative embodiment of the present invention, lipophilic cationic complexes of paramagnetic metal ions such as Gd, Dys, Fe, or Mn can be coadministered with agents that decrease the intramembrane potential. Complexes of paramagnetic metal ions produce relaxation enhancement of tissues placed within a strong magnetic field. Since relaxation enhancement is proportional to the local concentration of the paramagnetic metal complex, tissue relaxation differences can be augmented by use of the present invention during diagnostic tests with magnetic resonance imaging technology.

In another alternative embodiment of the present invention, lipophilic cation complexes of rhenium, in particular, but not limited to hexakis (akylisonitrile) rhenium(I) complexes, can be co-administered with agents that decrease the intramembrane potential. Because rhenium can produce ionizing radiation in sufficient local quantities to serve as a therapeutic radiopharmaceutical, the present invention can enhance tissue accumulation of the agent and improve its potential use in tumor therapy.

In a specific in vivo embodiment, TPB (3.6×10$^{-7}$ moles) in dimethyl sulfoxide is injected directly into the jugular vein of a rat within 30 seconds prior to the injection of Tc-MIBI (75$\mu$ Curies; approximately 6 pmoles/mCi).

In a specific in vitro embodiment of the present invention a combination of Tc-MIBI and TPB is administered in vitro to spontaneously contractile chick ventricular myocardial cells obtained from 10 day old chick embryo hearts disaggregated with trypsin. The optimal concentration range of TPB in this method is 3×10$^{-6}$M to 3×10$^{-5}$M. In further disclosed embodiments, Tc-MIBI net accumulation in the chick myocardial cells is enhanced by the addition of 10$^{-4}$M phloretin or 10$^{-4}$M 8-anilino-1-naphthalene sulfonic acid.

In alternative embodiments of the present methods, cells in vitro may be exposed to a combination of Tc-MIBI and either phloretin (10$^{-4}$M) or 8-amilino-1-naphthalene sulfonic acid (10$^{-4}$M). In further embodiments, these cells may be exposed to any combination of a hexakis(alkylisonitrile)technetium(I) complex and an agent that decreases the intramembrane potential. The agents include lipophilic anions and dipolar compounds such as described above.

In further embodiments of the present methods, the preferred and alternative compositions may be administered to any cell type in vitro. Cell types include prokaryotic and eukaryotic cells that contain membranes which undergo a decrease in intramembrane potential in response to the administration of the agents of the invention.

The in vitro methods are useful for imaging a specific cell type. Such imaging can be used, for example, to distinguish a specific cell type among a mixture of cells. In such methods each cell type in the mixture contains membranes that respond to the reducing agent with a specific quantitative alteration in membrane potential. Administration of labelled Tc complex and a reducing agent will thus result in a mixture of cell types wherein each cell type contains a characteristic amount of the labelled complex. The cell type can thus be distinguished by detecting and quantifying the label. This type of approach may be quantitative or qualitative.

The in vitro methods are also useful for the assay of agents that affect the intramembrane potential. The net accumulation of Tc-MIBI may be used as a measure of the alteration of potential that occurs in response to the exposure of a cell to a given agent.

Concentrations of TPB, phloretin, and 8-ANS that are useful in vivo and in vitro would be approximately 0.5 $\mu$M to 3 $\mu$M in the solutions immediately bathing the cells or tissues.

By "organometallic is intended, for the purpose of this invention, a metal bound through either a covalent or coordinate bond to a carbon-containing ligand or chelate. The person of ordinary skill in the art will readily recognize such covalently or coordinately bonded metalo-organic compounds. These compounds are discussed extensively in Cotton, F. A. and Wilkinson, G. *Advanced Inorganic Chemistry* Third Edition, Interscience Publishers, New York (1966).

By "lipophilic" cation is intended, for the purpose of this invention, a cationic complex with an octanol/water partition coefficient greater than 0.5.

By the term "treating" is intended the administration to subjects of the compositions of the invention for purposes which include prophylaxis, amelioration, or cure of disease.

By the term "administer" is intended any method for introducing the compositions of the present invention into a subject. Typical methods include, but are not limited to, oral, intranasal, parenteral (intravenous, intramuscular, or subcutaneous), or rectal. When administration is for the purpose of treatment, administration may be for either a "prophylactic" or "therapeutic" purpose. When provided prophylactically, the substance is provided in advance of any symptom. The prophylactic administration of the substance serves to prevent or attenuate any subsequent symptom. When provided therapeutically, the substance is provided at (or shortly after) the onset of a symptom. The therapeutic administration of the substance serves to attenuate any actual symptom. The administration may also be for diagnostic purposes. The term "administer" also relates to the application of a substance ex vivo as in cell or organ culture.

By the term "coadminister" is intended that each of at least two components be administered during a time frame wherein the respective periods of biological activity overlap. Thus the term includes sequential as well as coextensive administration of the compounds of the present invention.

By the term "animal" is intended any living creature that contains cells in which the intramembrane potential is reduced by the administration of agents of this invention. Foremost among such animals are humans; however, the invention is not intended to be so-limiting, it being within the contempletion of the present invention to apply the compositions of the invention to any and all animals which may experience the benefits of the application.

By "intramembrane potential" is meant the mean free energy difference for a hydrophobic ion within an aqueous-lipic bilayer that serves as a barrier to transmembrane transport of said ion. This potential is to be distinguished from the transmembrane potential that results from differential ion distribution from the extracellular space to the intracytoplasmic space.

By "decrease" is intended, for the purpose of this invention, a lowering of the net positive potential within a biological membrane in a cell.

By "accumulation" is intended, for the purposes of this invention, the net uptake and retention, within a cell, of the organometallic complexes of this invention.

By "enhance" is intended, for the purposes of this invention, an increase in accumulation of organometallic complexes in living cells, such that the complexes are accumulated to levels that are in excess of those levels that are attained in the absence of the enhancing agent.

By the term "disease" is intended any deviation from or interruption of the normal structure or function of any part, organ, or system (or combination thereof) of the body that is manifested by a characteristic set of symptoms and signs.

By "label" is intended any atom or compound associated with a lipophilic cationic organometallic complex such that the complex can be located and quantitated. The association can be by means of covalent bonds, all means of non-covalent bonds, and any means of non-covalent attractive forces. The label may be intrinsic (found within the molecule per se, such as a radioisotopic form of an element) or extrinsic (found attached to the molecule as by a covalent bond or associated with the molecule as by non-covalent bonds or other non-covalent attractive chemical forces). Examples of types of labels which can be used in the present invention include, but are not limited to, enzyme labels, radioisotopic labels, non-radioactive isotopic labels, fluorescent labels, toxin labels, and chemiluminescent labels.

By "pharmaceutical compound" is intended a chemical entity, whether in the solid, liquid, or gaseous phase, which entity may be used on or administered to animals, including humans, as an aid in the diagnosis, treatment, or prevention of disease or other abnormal condition, for the relief of pain or suffering, or to control or improve any physiologic or pathologic condition. The term 'compound' should be read to include synthetic compounds, natural products and macromolecular entities such as polypeptides, polynucleotides, or lipids and also small entities such as neurotransmitters, ligands, hormones or elemental compounds. The term "compound" is meant to refer to that compound whether it is in a crude mixture or purified and isolated. The term "pharmaceutical" should be read to include any and all compounds that may be used as defined above.

By "alkyl" is intended, for the purpose of this invention, any functional group of the general formula $-CR_3$ where R can be identical or different and include the elements H, C, N, O, S, F, Cl, Br, and I. Representative structures include, but are not limited to, substituents consisting of $-CH_3$, $-CH_2CH_3$, $CH(CH_3)_2$, $-C(CH_3)_3$, $-C(CH_3)_2$ $OCH_3$, $-C(CH_3)_2$ $COOCH_3$, $-C(CH_3)_2$ $OCOCH_3$ $-C(CH_3)CONH_2$, $-C_6H_5$, $-CH_2(C_6H_4)OH$, or any of their isomeric forms having the general composition as the isonitrile radionuclide complexes in U.S. Pat. No. 4,452,774 which is incorporated herein by reference.

EXAMPLES

Example 1

Experimental Solutions

Control buffer was a modified Earle's balanced salt solution (MEBSS) with the following composition (mN) $Na^{30}$, 145; $K^+$, 5.4; $Ca^2$, 1.2; $Mg^{2+}$, 0.8; Cl, 152; $H_2PO_4$, 0.8; $SO_4^{2-}$, 0.8; dextrose, 5.6; HEPES, 4.0; and bovine calf serum, 1% (v/v); pH 78.4±0.05; 37° C. K-methanesulfonate was made by titration of methanesulfonic acid with KOH (Piwnica-Worms, D., et al., *J. Gen. Physiol.* 81:731–748 (1983)) and replaced NaCl in some solutions by equimolar substitution where indicated. Natetraphenylborate, CCCP, bumetanide and valinomycin were dissolved into DMSO prior to addition to buffer. DMSO alone has no significant affect on contractile activity, action potential configuration (Lieberman, M., et al., *Dev. Biol.* 31:380–403 (1973)) or Tc-MIBI uptake kinetics (Piwnica-Worms, D., et al., *Circ.* (in press)).

The K concentration of selected buffers was determined by atomic adsorption spectrophotometry (Model 3030, Perkin-Elmer, Norwalk, Conn.) as described (Piwnica-Worms, D., et al., *Circ.* (in press)).

Synthesis of the radiolabeled compound [$^{99m}$Tc]MIBI was performed using a one-step kit developed at duPont Medical Products, Billerica, Mass. The kit reaction vial contains the isonitrile ligand in the form of tetrakis (2-methoxy isobutyl isonitrile) Copper (I) tetrafluoroborate (1.0 mg), a stannous chloride reducing agent (0.075 mg L-cysteine hydrochloride (1.0 mg), Sodium Citrate (2.6 mg) and Mannitol (20. mg). The intrinsically radiolabelled complex was formed by adding [$^{99M}$Tc]TcO$_4$− (20–30 mCi, 2–25 pmol/mCi) in 1–2 ml saline (0.15M, NaCl), obtained from a commercial molybdenum/technetium generator (duPont Medical Products, Billerica, Mass.), to the kit reaction vial, heating at 100° C. for 15 min, and allowing to cool to room temperature producing an almost quantitative yield of the [$^{99m}$Tc](MIBI)$_6$+ complex. Excess reducing agent and starting materials were separated from the radiolabelled component as follows: the contents of the reaction vial were loaded via syringe onto a reversed phase Sep-Pak cartridge (C-18, Waters Assoc., Milford, Mass.) pre-wet with ethanol (3 ml, 90%) followed by distilled water (5 ml). Hydrophilic impurities were eluted from the cartridge by washing with saline (10 ml, 0.15M) and the desired Tc-MIBI collected by elution with ethanol/saline (2 ml; 9:1, v:v). Final total $^{99m}$Tc activity in the 2 ml effluent (stock) was assayed in a standard dose calibrator (CRC-12, Capintec, Ramsey, N.J.). Radiochemical purity was found to be greater than 97% by thin layer chromatography (aluminum oxide plates, J. T. Baker, Phillipsburg, N.J.) using ethanol (absolute) as the mobile phase.

Statistics

Values are presented as mean ±SEM. Statistical significance was determined by the two-tailed unpaired Student's t test where indicated in the text (Wallenstein, S., et al., Circ. Res. 47:1–9 (1980)).

Example 2

Tissue culture of Chick Myocardial Cells

Monolayers of spontaneously contractile chick ventricular myocardial cells were obtained from disaggregated 10-day old chick embryo hearts by a slight modification of previously published methods (Horres, C. R., et al., In Pinson, A. (ed.), The Heart Cell in Culture, Boca Raton, CRC Press, pp. 77–108 (1987)). Hearts were trimmed of connective tissue and atria, finely minced and serially exposed to 0.024% (w/v) trypsin in $Ca^{2+}$- and $Mg^{2+}$- free Earle's salt solution for 7 minutes at 37° C. Gentle trituration and agitation on an orbital shaker bath aided disaggregation. Cells released from the first exposure were discarded and cells aspirated from the next four exposures were then added to an equal volume of trypsin deactivating solution consisting of ice-cold culture medium. Cells were centrifuged at 400 g for 10 minutes, resuspended and combined in culture medium, counted with a hemocytometer and diluted to yield a suspension of $5 \times 10^5$ cells/ml. 12 ml of suspension were incubated in 100 mm plastic culture dishes containing 7 coverslips (25 mm diameter) placed on the bottom of each dish to serve as substrate for cell growth. Cells were maintained in a humidified atmosphere of 5% $CO_2$/95% air for 3–4 days yielding a confluent layer of spontaneously contractile myocytes on each coverslip.

Example 3

Radiotracer Uptake Methods

Radioactive uptake methods have been described in detail (Piwnica-Worms, D., et al, Circ. (in press). Briefly, coverslips with confluent cells were removed from culture media and pre-equilibrated for 40–60 seconds in MEBSS buffer. Uptake and retention experiments were initiated by immersion of coverslips in 60 mm glass Pyrex dishes containing loading solution consisting of buffer with 0.1–0.6 nM [$^{99m}$Tc-MIBI] (0.01–0.4 Ci/nmole; 25–100 uCi/ml). Preparations were removed at various times and rinsed three times in 25 ml volumes of ice-cold (2° C.) isotope-free buffer for 8 seconds each to clear extracellular spaces. Preparations and aliquots of the loading buffer and stock solutions were counted in a well-type sodium iodide gamma counter after which cell protein on each coverslip was extracted in 1% sodium dodecylsulfate with 10 mM sodium borate and assayed by the method of Lowry (Lowry, O. H., et al., J. Biol. Chem. 193:265-275 (1951)). Tc-MIBI binding to glass coverslips without cells was used as an estimate of non-specific adhesion to the substrate (<% of total activity obtained with cellular preparations); this value was subtracted from total uptake determinations to derive the cell-associated counts. Use of generator equilibrium equations (Lamson, M. L., et al., i J. Nucl. Med. 16:639–641 (1975)) allowed calculation of absolute moles of Tc-MIBI in solutions and preparations. Results were therefore expressed as fmol cellular Tc-MIBI/mg protein per nM extracellular Tc-MIBI concentration. Division of this value by the cell water space (6.9 ul/mg protein; Chiu, M. L., et al., J. Nucl. Med. (31:1646–1653(1990)) yields a nominal intracellular/extracellular Tc-MIBI accumulation ratio neglecting subcellular compartmentation of the agent.

Example 4

Effect of TPB on Net Accumulation of Tc-MIBI in Cultured Chick Heart Cells

Figure 2:
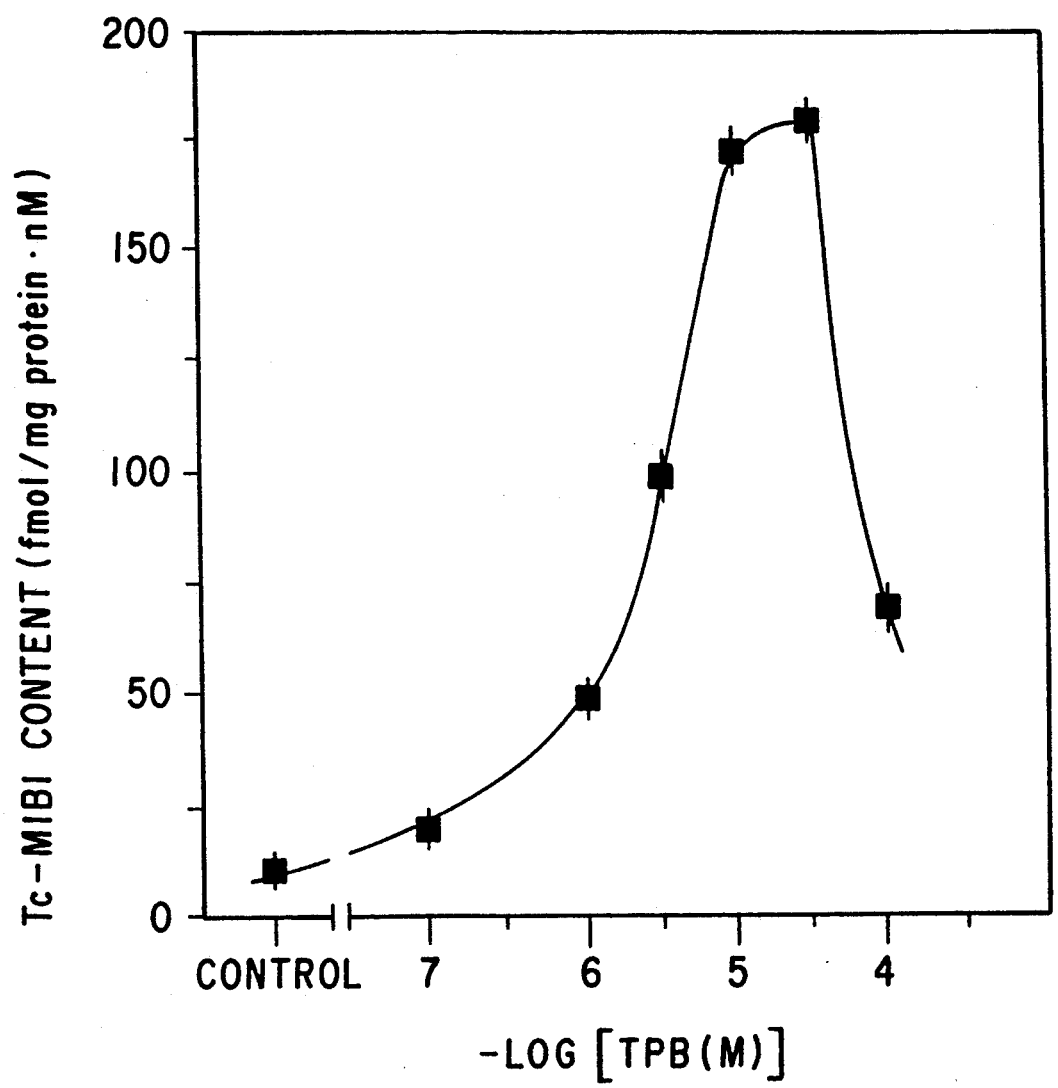
FIG. 2. Concentration-effect curve for TPB enhancement of 2-minute uptake of Tc-MIBI. Preparations were pre-incubated for 1 minute in control MEBSS buffer containing TPB at the indicated concentrations prior to determination of tracer Tc-MIBI uptake in the continued presence of TPB. Each point represents the mean ±SEM of 3 determinations.

Myocytes incubated in MEBSS containing Tc-MIBI (0.5 nM) accumulated the lipophilic cation to an apparent equilibrium. A low concentration of tetraphenylborate (TPB, $10^{-9}$M) minimally increased the rate of Tc-MIBI accumulation, but did not significantly affect final equilibrium content (P >0.5). However, at concentrations equal or greater than $5 \times 10^{-7}$M, TPB increased both maximal accumulation and the uptake kinetics of Tc-MIBI (FIG. 1). In $10^{-5}$M TPB, peak accumulation of Tc-MIBI was 4-fold greater than control (P <0.001) and occurred within 10-20 minutes, 3-fold faster than control. At these high concentrations of TPB, accumulation of Tc-MIBI was not constant over time, but rather declined after achieving a transient maximum value. A concentration-effect curve for TPB enhancement of myocellular uptake of Tc-MIBI is shown in FIG. 2. TPB increased myocellular uptake of Tc-MIBI in a concentration-dependent manner up to $3 \times 10^{-5}$M (half-maximal concentration $3 \times 10^{-6}$M); higher concentrations of the lipophilic anion markedly reduced net cellular accumulation of Tc-MIBI.

Example 5

Effect of MSA on Tc-MIBI Net Accumulation

Figure 3:
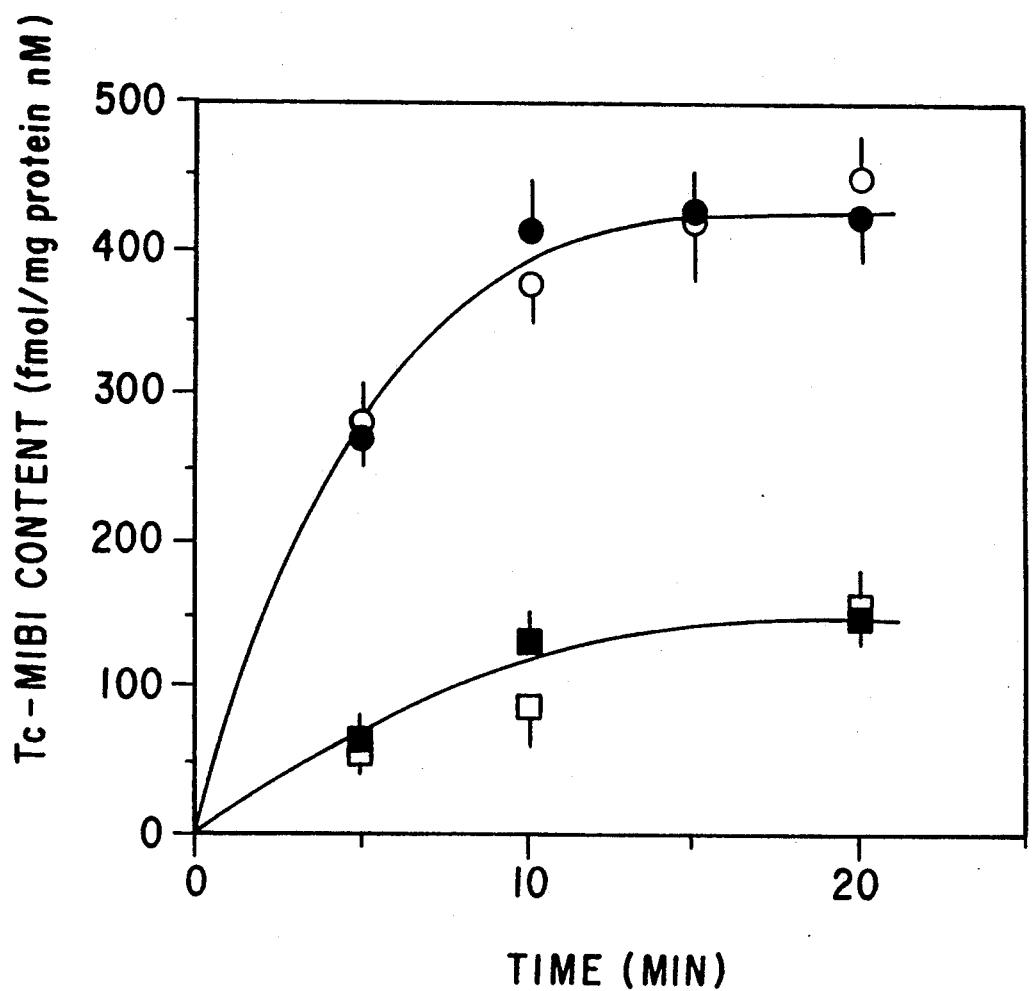
FIG. 3. Effect of MSA on Tc-MIBI net accumulation. Preparations were incubated for the times indicated in Tc-MIBI loading buffer containing 5.4 mM KCl (□, ○) or 5.4 mM K-MSA (■, ·; prepared by equimolar substitution of K-MSA KCl) in the absence (□, ■) or presence (○, ·) of TPB ($10^{-5}$M). Each point represents the mean ±SEM of 3 determinations.

As opposed to TPB, relatively high concentrations of the impermeant anion methanesulfonate (MSA; 5.4 mM) (Piwnica-Worms, D., et al., *J. Gen. Physiol.* 81:731–748 (1983)) did not significantly alter uptake kinetics or equilibrium content of Tc-MIBI (FIG. 3). Furthermore, 5.4 mM MSA did not interfere with the TPB-induced enhancement of Tc-MIBI accumulation (FIG. 3). Even 130 mM MSA had little effect on Tc-MIBI uptake in the presence of TPB ($10^{-5}$M) and 130 mM K. (130 mM KCl buffer+bumetamide [$10^{-5}$M]: 63.7±3.2 fmol Tc-MIBI/mg protein per nM vs. 130 mM K-MSA buffer: 79.3±1.1; n=3; P=0.01).

Example 6

Influence of TPB on Membrane Potential-Independent Accumulation of Tc-MIBI

Figure 4:
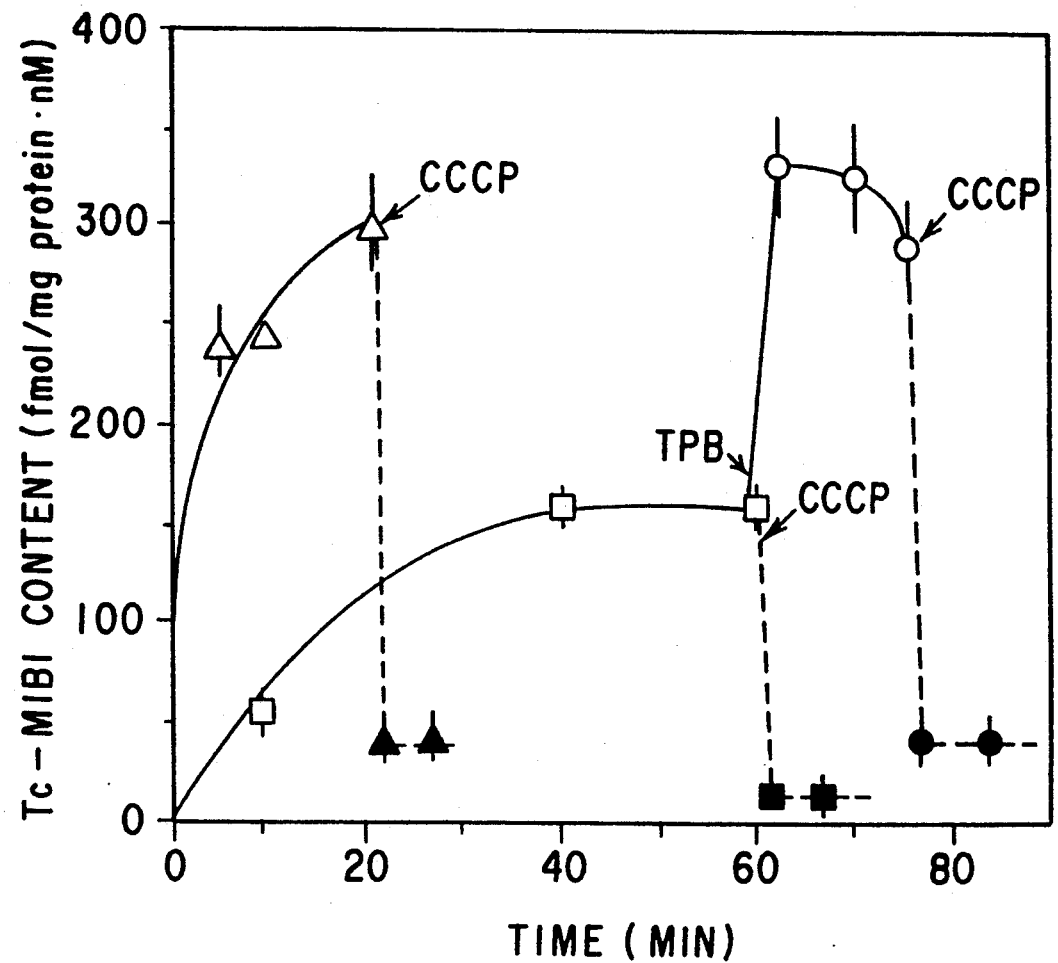
FIG. 4. Effect of the mitochondrial uncoupler CCCP ($5 \times 10^{-6}$M) on enhancement of Tc-MIBI accumulation by TPB ($10^{-5}$M). Preparations were incubated for the times indicated in 5.4 mM $K_o$ control loading buffer containing tracer Tc-MIBI and TPB together (△) or in loading buffer containing Tc-MIBI alone (□). For the latter incubation, TPB was added to the loading buffer at the arrow and cell content of Tc-MIBI subsequently determined (○). Under each condition, CCCP was added to the loading buffers as indicated by the arrows and cell content of Tc-MIBI determined (▲, ■, ·). Each point is the mean ±SEM of 3 determinations.

To determine whether TPB was increasing membrane partitioning (adsorption) of Tc-MIBI or enhancing a potential-dependent component of net uptake of Tc-MIBI, cells were exposed to various sequential combinations of Tc-MIBI, TPB and the protonophore CCCP. As shown in FIG. 4, TPB ($10^{-5}$M) increased myocyte content of Tc-MIBI to similar values above control whether added to the buffer at time zero or subsequent to the attainment of a Tc MIBI plateau. The time of onset for TPB enhancement of Tc-MIBI was rapid. Augmentation of Tc-MIBI myocellular kinetics could be detected as early as 5 seconds into a pre-incubation period with TPB (control: 1.23±0.15 fmol Tc-MIBI/mg protein per nM; $+10^{-7}$M TPB: 3.37±0.57; $+5\times10^{-6}$M TPB: 20.6±0.43; 2 min uptakes with n=3-4 each). Depolarizing mitochondiral membrane potentials with CCCP (5 uM) caused the rapid and near complete release of myocellular Tc-MIBI both in the presence and absence of TPB (P<0.001). The CCCP-insensitive retention of Tc-MIBI was slightly higher in TPB-treated cells. This could reflect either increased lipid partitioning of Tc-MIBI in the presence of TPB or differential effects of TPB on membrane potentials under these conditions.

To further explore the influence of TPB on any potential-independent accumulation of Tc-MIBI in myocytes, preparations were exposed to 130 mM K° 20 mM Cl$_o$ buffer (Table 1). Intracellular potassium (K$_i$) in these preparations has been previously determined to be 130 mM (Piwnica-Worms, D., et al., *Circ.* (in press)), therefore equalizing the transmembrane K concentration with this buffer produces an isovolumic depolarization of plasma membrane potential to nearly zero millivolts (Horres, C. R., et al., *Am. J. Physiol.* (*Cell*) 236:C163–C170 (1979)). The residual uptake of Tc-MIBI in high K. buffer could be attributed to intact mitochondrial membrane potentials since collapsing mitochondrial potentials with valinomycin (1 ug/ml) eliminated net accumulation of Tc-MIBI (Table 1). TPB ($10^{-5}$M) increased myocellular content of Tc-MIBI in high K. buffer, but again, this augmentation was completely valinomycin-sensitive. Equilibration of intracellular and extracellular spaces occurred in the presence of high K buffer plus valinomycin under all conditions (in/out ration ~1; P=NS) indicating the lack of any significant potential-independent membrane binding of Tc-MIBI.

TABLE 1

Effect of Valinomycin on Tetraphenylborate Enhancement of Tc-MIBI Accumulation in High K$_o$ Buffer

| Buffer | Tc-MIBI Net Uptake (fmol/mg protein/nM$_o$) | | Tc-MIBI$_i$/ Tc-MIBI$_o$ |
|---|---|---|---|
| 130 K$_o$ | 65.3 ± 5.3 | (n = 3) | 9.5 |
| 130 K$_o$ + TPB | +93.9 ± 4.4 | (n = 3) | 13.6 |
| 130 K$_o$ + val | *6.2 ± 0.3 | (n = 3) | 0.9 |
| 130 K$_o$ + TPB + val | *7.6 ± 0.8 | (n = 3) | 1.1 |

Preparations were incubated in high K$_o$ low Cl$_o$ loading buffer +/− valinomycin (1 ug/ml) for 20 minutes in the presence of TPB ($10^{-5}$M) or for 40 minutes in its absence to determine peak accumulation of Tc-MIBI under each condition. Values are the mean ±SEM. Tc-MIBI in/out ratios were obtained by dividing net uptake values by the cell water space of 6.9 ul/ug protein (Chiu, M. L., et al., *J. Nucl.* 31:1646–1653 (1990)). +p<0.01; * p<0.001 compared to net uptake in 130 mM K$_o$ buffer.

Example 7

K$_o$-Dependence of Tc-MIBI Net Uptake in the Absence and Presence of TPB

Figure 5:
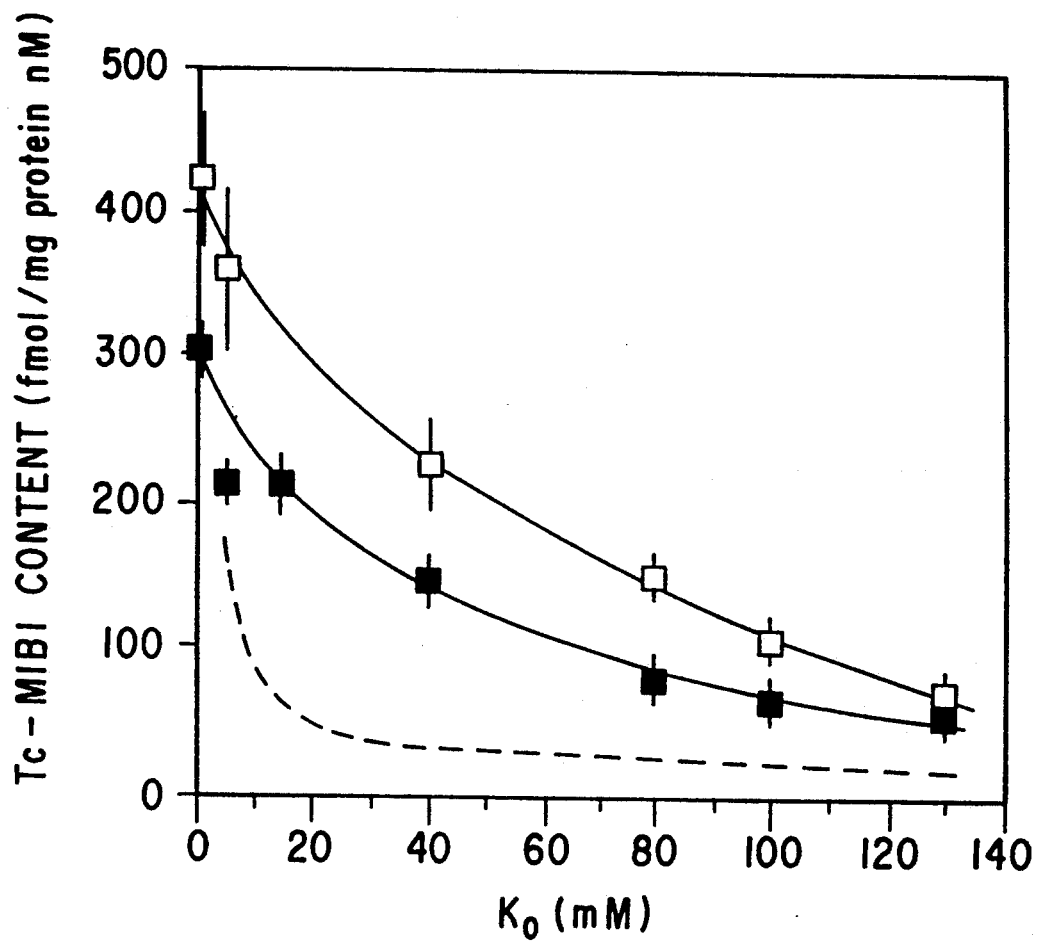
FIG. 5. $K_o$-dependence of Tc-MIBI net uptake in the absence (■) and presence (□) of TPB ($10^{-5}$M). Peak accumulation of Tc-MIBI was determined in preparations incubated in loading buffers containing the indicated $K_o$ (equimolar replacement of NaCl by KCl) for 40 minutes (control) or for 20 minutes (+TPB). $K_o$-induced cell volume changes were prevented by addition of bumetanide ($10^{-5}$M) to each buffer. Each point is the mean ±SEM of 3 determinations. Solid lines have no theoretical significance. The dashed line represents the Tc-MIBI content expected at each $K_o$ assuming an intracellular/extracellular Tc-MIBI concentration ratio equal to the $K_i/K_o$ ratio. $K_i = 130$ mM (Piwnica-Worms, D., et al., Circ. (in press)).

The myocellular plasma membrane potential is primarily a K diffusion potential for K. >10 mM (Horres, C. R., et al., *Am. J. Physiol.* (*Cell*) 236:C163–C170 (1979)); consistent with this, we observed a strong dependence of Tc-MIBI net uptake on K. (FIG. 5). TPB increased Tc-MIBI net accumulation at all K. concentrations and the K.-dependence of Tc-MIBI uptake was preserved. Possible K.-induced cell volume changes could not have significantly contributed to net uptake of Tc-MIBI; no differences were found between use of low [Cl]. (K-MSA substitution for NaCl) or use of bumetanide ($10^{-5}$M) (an inhibitor of the volume-responsive Na+K+2Cl co-transporter (26) during KCl substitution for NaCl) to maintain cells isovolumic in various K. buffers (data not shown). Nominal intracellular/extracellular accumulation ratios, calculated by dividing the Tc-MIBI content values in FIG. 5 by the previously determined cell water of 6.9 ul/mg protein (Chiu, M. L., et al., *J. Nucl.* 31:1646–1653(1990)), were greater than those expected from the K$_i$/K$_o$ ratios in the absence of TPB; this effect was even more pronounced in the presence of TBP. This provided further evidence for enhanced subcellular compartmentation of Tc-MIBI by TPB.

Example 8

Effect of TPB on the K$_o$-Dependence of Tc-MIBI Influx Rates

Figure 6A:
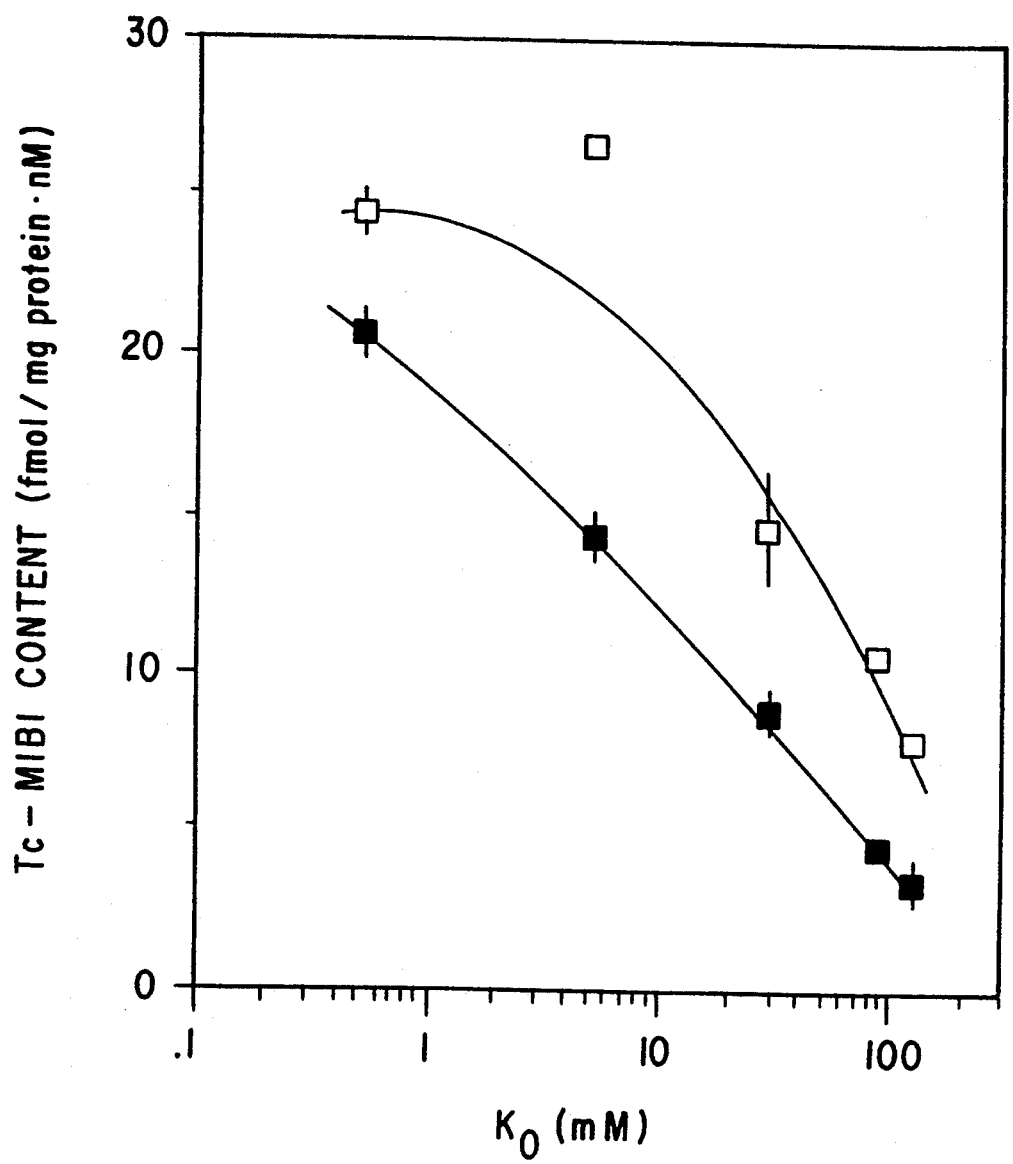
FIG. 6. Effect of TPB on the $K_o$-dependence of Tc-MIBI influx rates. A) Preparations were preincubated in MEBSS containing the indicated $K_o$ (K-MSA substitution for NaCl) for 1 minute in the absence (□) and for 5 minutes in the presence (■) of valinomycin (1 ug/ml) prior to determination of 2-min Tc-MIBI uptakes in buffer of the same composition. B) Same conditions as A with a 5-minute pre-incubation period in buffers that also contained TPB ($10^{-5}$M) in the absence (○) or presence (·) of valinomycin. C) Resting membrane potential ($E_m$) as a function of $K_o$. $E_m$ was calculated from the Tc-MIBI influx data shown in A in the presence of valinomycin using the Goldman flux equation (Restrepo, D., et al., J. Gen. Physiol. 92:489-507 (1988)): $J/J_o = -x/(1-e^x)$ where $x = E_m F/RT$ and $J/J_o$ is the ratio of Tc-MIBI influx rates at $E_m$ and zero membrane potential ($K_o = 130$ mM), respectively. RT/F equals 26 mV at 37° C. The solid lines in A and B have no theoretical significance. The solid line in C represents a linear regression of the data: $-E_m = -67$ log $K_o + 147$mV ($r = -0.99$). The dashed line in C represents the calculated K diffusion potential (Nernst) for $K_i = 130$ mM. Each point is the mean ±SEM of 3 determinations.
Figure 6B:
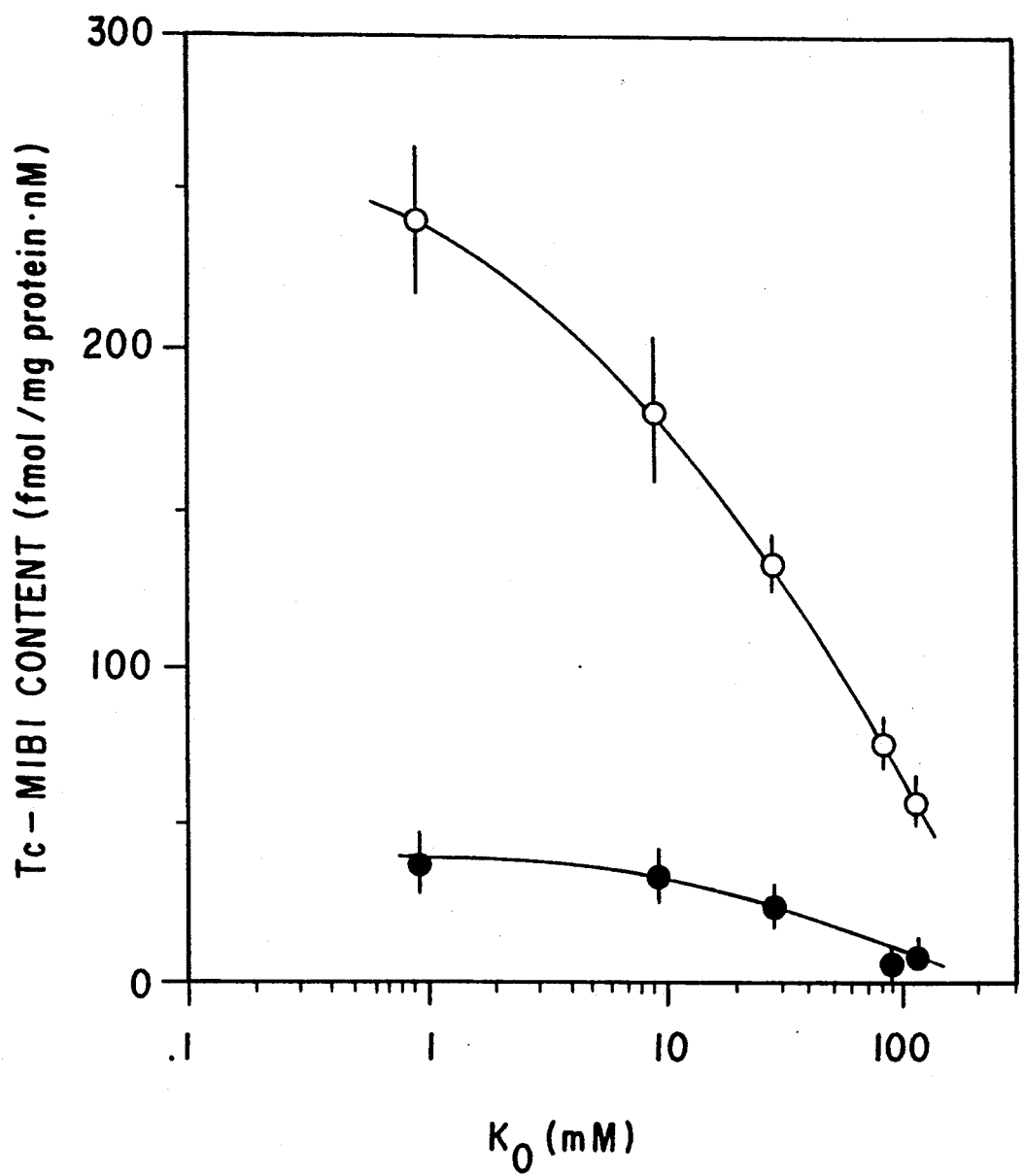
Figure 6C:
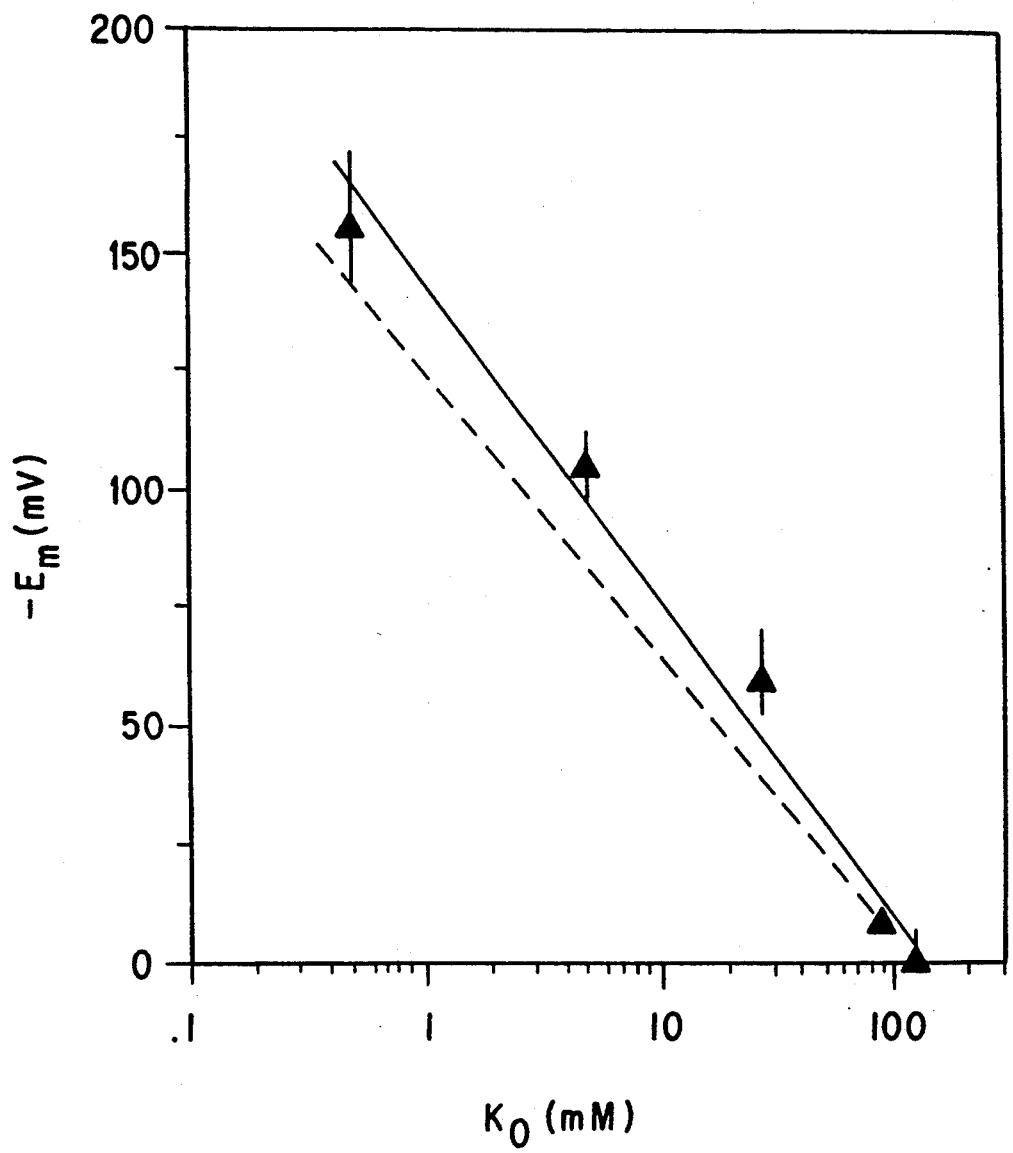

Unidirection influx of Tc-MIBI into heart cells determined by 2 min uptake values was strongly K$_o$-dependent, (FIG. 6B). Control experiments indicated that complete onset of the valinomycin-induced depolarization of mitochondrial potentials required approximately a 3 min pre-incubation period (data not shown). Therefore, preparations were pre-treated in valinomycin (1 ug/ml) for 5 minutes prior to determination of Tc-MIBI influx; use of the Goldman flux equation (Restrepo, D., et al., *J. Gen. Physiol.* 92:489–507 (1988)) allowed estimation of the plasma membrane potential as a function of K$_o$ (FIG. 6C). As can be seen, Tc-MIBI approximated a Nernstian probe of plasma membrane potential under these conditions (slope=$-67$ mV/decade; r=$-0.99$). Whereas Tc-MIBI influx in the absence of TPB was only modestly valinomycin-sensitive (FIG. 6A), Tc-MIBI influx in its presence was highly valinomycin-sensitive (FIG. 6B), implying enhanced mitochondrial uptake of Tc-MIBI by TPB.

Example 9

Effect of Dipolar Compounds on Net Uptake of Tc-MIBI

Figure 7:
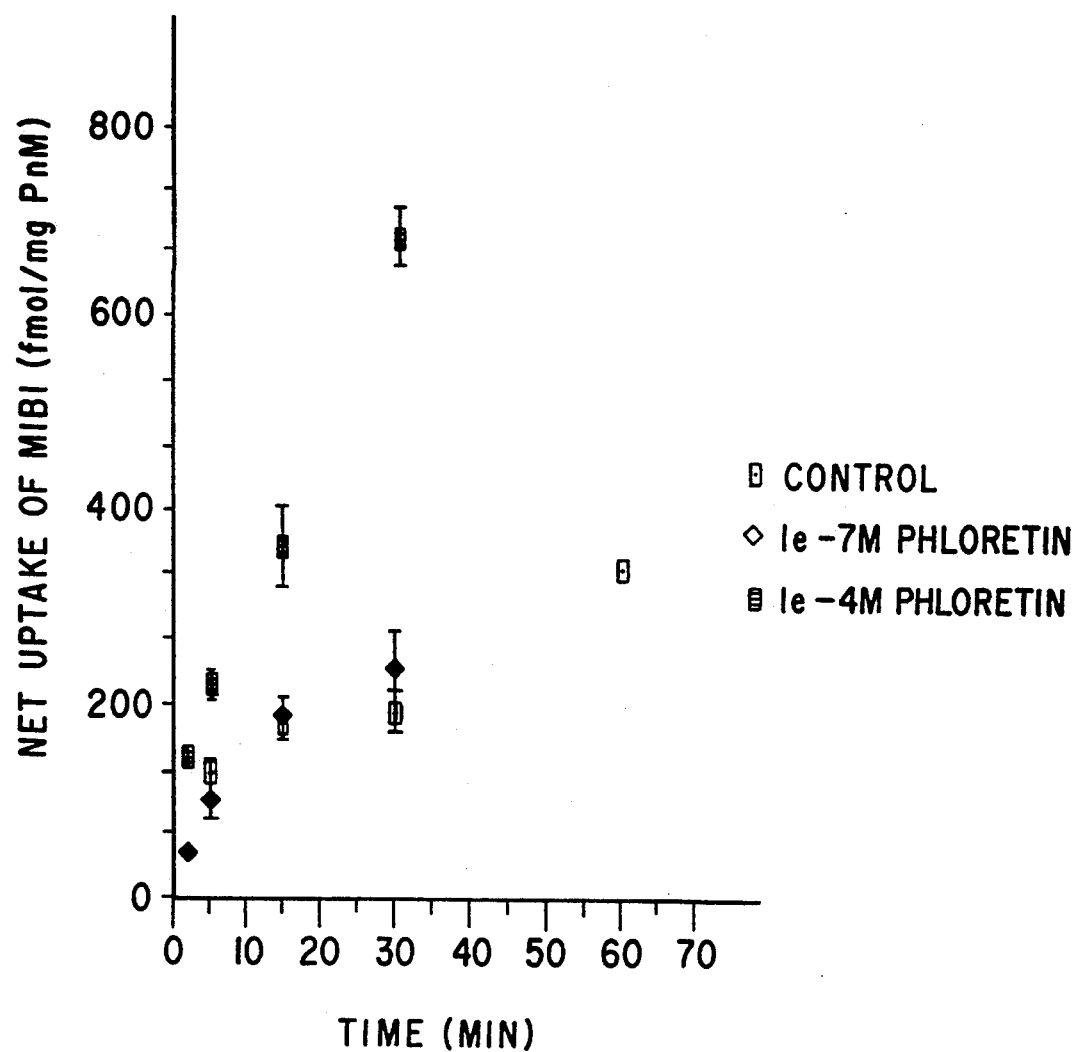
FIG. 7. Effect of phloretin on net accumulation of Tc-MlBl in cultured heart cells. Preparations were incubated for the times indicated in Tc-MIBI loading buffer in the absence (□) or presence of phloretin (◆, $10^{-7}$M; ■, $10^{-4}$M). Each point represents the mean ±SEM of 3-4 determinations.
Figure 8A:
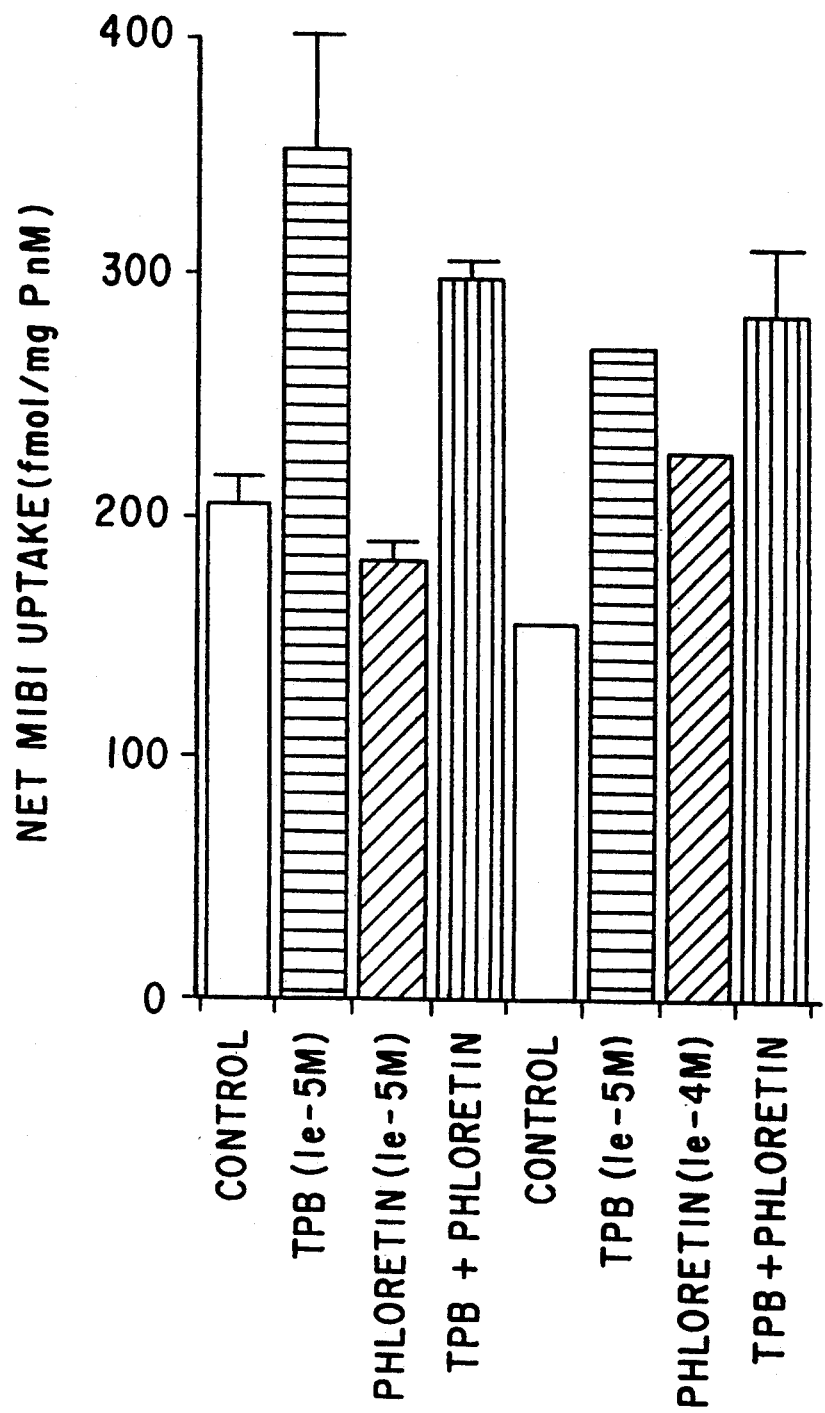
FIG. 8. Effect of phloretin and tetraphenylborate together on net uptake of Tc-MB1 in cultured chick heart cells. Preparations were incubated in MEBSS containing Tc-MIBI for 30 minutes in the absence (control) or presence of tetraphenylborate and phloretin each alone or in combination as indicated on the abscissa. Each group of four conditions (two groups in A and one group in B) represent separate cultures. Error bars indicate ±SEM for three or more determinations. There is no evidence of additive enhancement by tetraphenylborate and phloretin.
Figure 8B:
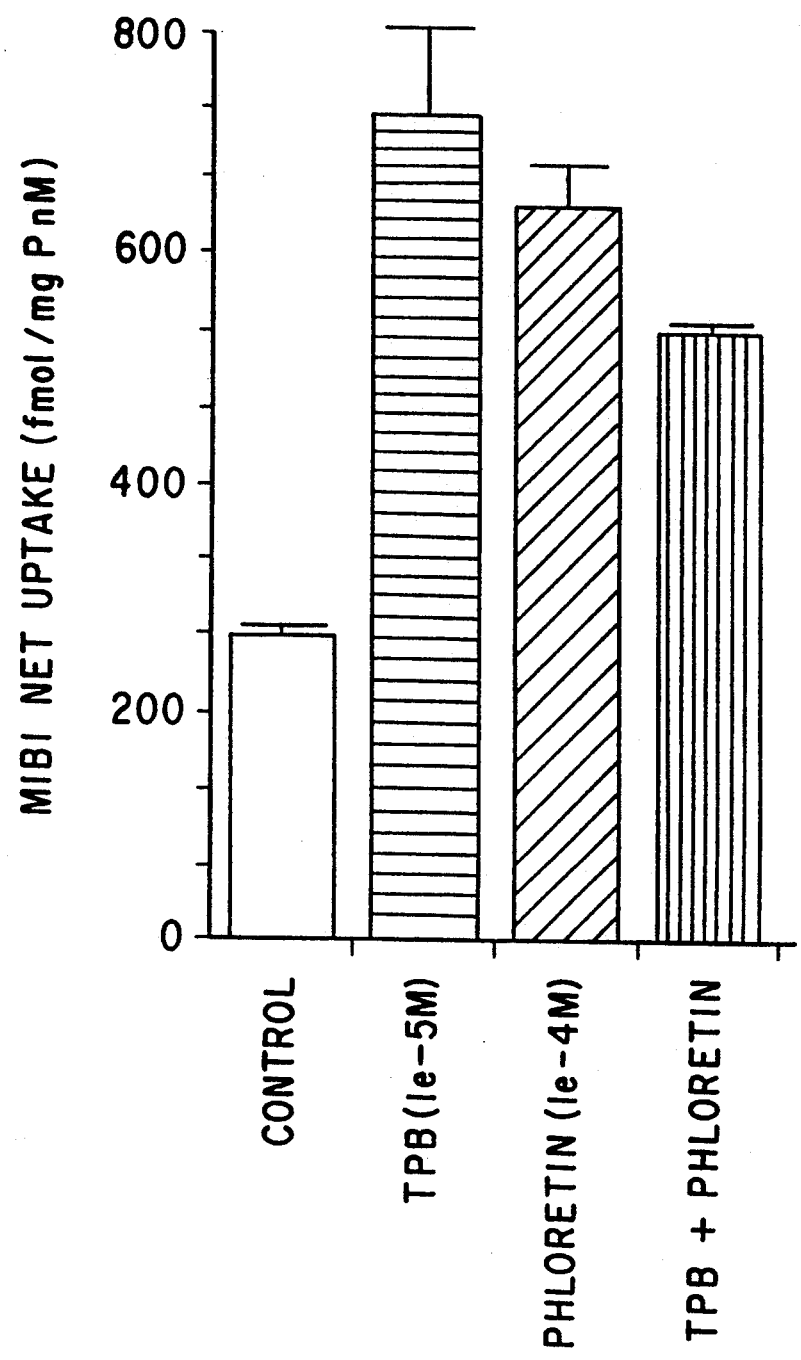

The effect, on Tc-MIBI accumulation, of dipolar compounds that decrease the intramembrane potential was investigated in cultured chick myocardial cells that were prepared by the disaggregation of 10 day old embryos. The time course and dose response of phloretin is shown in FIG. 7. At a concentration of $10^{-4}$M phloretin, within 30 minutes of administration, the net uptake of Tc-MIBI is enhanced five-fold above the control. FIG. 8 shows the results of several experiments in which 30 minute uptake levels of Tc-MIBI were measured. The uptake was measured in the presence of $10^{-4}$M and $10^{-5}$M phloretin with or without $10^{-5}$M TPB. In the presence of $10^{-4}$M phloretin, the net retention of Tc-MIBI ranges from approximately 2.5-3.5-fold above the control levels.

Figure 9:
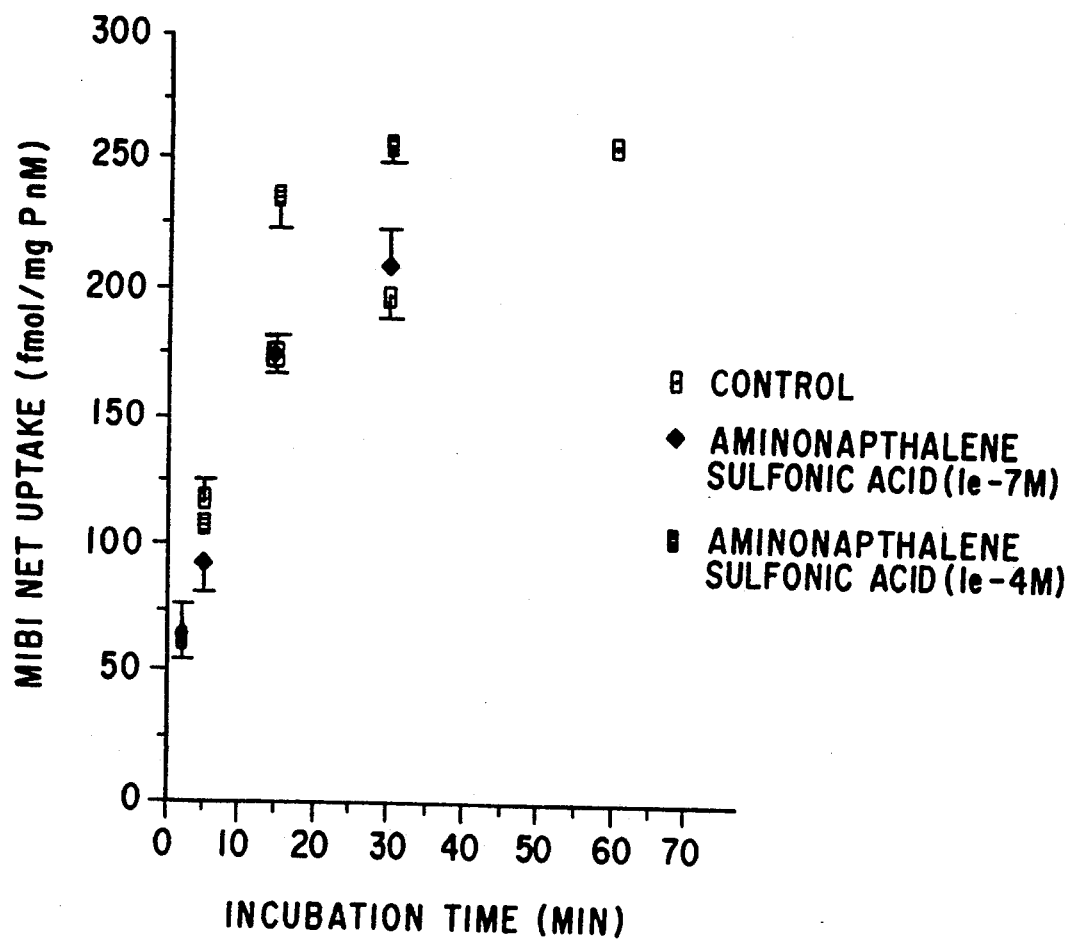
FIG. 9. Effect of 8-anilino-1-naphthalene sulfonic acid on net uptake of Tc-M1B1 in cultured chick heart cells. Preparations were incubated for the times indicated in Tc-MIBI loading buffer in the absence (□) and presence of 8-ANS (♦, $10^{-7}$M; ■, $10^{-4}$M). Each point represents the mean ±SEM of 3-4 determinations.

FIG. 9 shows the net uptake of Tc-MIBI in response to dose and time of incubation with 8-anilino-1-naphthalene sulfonic acid. At a concentration of $10^{-4}$M and within 30 minutes, the net uptake of Tc-MIBI is enhanced 25% over the control.

Example 10

Effect of TPB on Tissue Uptake of Tc-MIBI in Animals

Table 2 shows the levels of uptake of Tc-MIBI in heart, blood, liver, kidney and lung of live rats in which TPB and Tc-MIBI were co-administered. The results are expressed as percent injected dose per gram of tissue. For liver, kidney, lung and blood there was a significant increase in Tc-MIBI accumulation within the tissues. For all tissues there was a 50% increase in tissue retention of Tc-MIBI from 6.04 to 9.15% ID per gram of total tissue. For this series of experiments, 50 microliters of dimethylsulfoxide lacking or containing 7.2 mM TPB were injected directly into the jugular vein of anesthetized rats immediately prior to the injection of Tc-MIBI (150 microliters; 100 microCuries per 200 microliters).

After 15 minutes, the animal was sacrificed by thoracotomy, organs extracted and placed in test tubes and counted for radioactivity in a standard well-type gamma counter. Tissue wet weights were obtained by subtracting fare weights from total weight of test tubes plus tissue.

Results are expressed as mean ±SEM of three determinations each.

TABLE 2

| EFFECT OF TETRAPHENYLBORATE ON THE BIODISTRIBUTION OF Tc-MIBI IN RATS | | |
|---|---|---|
| | % ID/gm | |
| Organ | −TPB | +TPB |
| Heart | 1.92 ± 0.51 | 1.45 ± 0.11 |
| Liver | 0.25 ± 0.15 | 0.76 ± 0.40 |
| Blood | 0.04 ± 0.01 | 0.06 ± 0.01 |
| Kidney | 3.38 ± 1.09 | 5.81 ± 0.74 |
| Lung | 0.45 ± 0.09 | 1.07 ± 0.15 |

Example 11

Physiological effects of modest TPB concentrations

Moderate concentrations of TPB produced a significant increase in final myocellular content of tracer Tc-MIBI in addition to an increase in Tc-MIBI kinetics. While not intending to be held to this interpretation, this augmented content of tracer Tc-MIBI appeared to be localized to the mitochondria. Evidence in support of this included: 1) The nominal myocellular accumulation ratio for equilibrium uptake of Tc-MIBI in the presence of TPB exceeded expectations for the plasma membrane potential (based upon a Nernstian distribution of the transmembrane K gradient), a finding consistent with enhanced compartmentalization of Tc-MIBI within mitochondria. 2) The majority of the TPB-enhanced net uptake of Tc-MIBI was releasable by the mitochondrial uncoupler CCCP. However, the residual CCCP-insensitive Tc-MIBI content, representing only 13% of the TPB-enhanced Tc-MIBI content, was slightly higher than the control residual. This suggests an increase in a component of potential-independent binding of tracer Tc-MIBI in the presence of TPB or TPB-induced changes in plasma membrane potentials. 3) However, virtually eliminating any contribution from the plasma membrane potential by incubating cells in 130 mM $K_o$ buffer (Piwnica-Worms, D., et al., *Am. J. Physiol. (Cell)* 249:C337–C344 (1985)) and collapsing mitochondrial potentials with valinomycin caused equilibration of intracellular and extracellular Tc-MIBI in both the presence and absence of TPB. Thus, there was no evidence of TPB-induced potential-independent membrane partitioning of tracer Tc-MIBI in myocytes under these conditions with moderate concentrations of TPB. (The membrane binding saturation of carrier-added Tc-MIBI discussed below occurs at $10^6$-fold higher concentrations.) Therefore, in sum, the plateau data indicated enhancement of mitochondrial localization of tracer Tc-MIBI in the presence of TPB.

It therefore follows that in the absence of TPB, Tc-MIBI does not completely equilibrate with the mitochondrial membrane potential and final myocyte Tc-MIBI content under control conditions may have represented only a quasi-equilibrium. In accord with the general model of hydrophobic ion transport discussed earlier, this may suggest that the mitochondrial intramembranous energy barrier is sufficiently positive to inhibit the ability of Tc-MIBI to attain maximum distribution ratios.

Toxicity

High TPB concentrations ($10^{-4}$M) produced relatively less enhancement of Tc-MIBI accumulation compared to moderate TPB concentrations suggesting cellular toxicity at high concentrations of the lipophilic anion. These data are compatible with the previously reported competitive displacement of tracer $^{99m}$Tc-MIBI by carrier $^{99}$Tc-MIBI at a half-maximal molar ratio (apparent $K_D$) of $7 \times 10^{-5}$ (Piwnica-Worms, D., et al., *J. Nucl. Med.* 31:464–472 (1990)), a result consistent with cellular toxicity at very high carrier-added concentrations of the lipophilic cation. Therefore, results from cultured heart cells may have demonstrated onset of binding saturation (and membrane disruption) for very high concentrations of these hydrophobic ions and are consistent with reports of electrostatic saturation of both TPB binding to egg phosphatidylcholine vesicles at $6 \times 10^{-4}$M (Flewelling, R. F., et al., *Biophys. J.* 49:531-540 (1986)) and TPB binding to bacterial phosphatidylethanolamine bilayers at concentrations exceeding $10^{-6}$M (Anderson, O. S., et al., *Biophys. J.* 21:35-70 (1978)).

Quantitative evaluation of membrane potential

The dominance of net cellular accumulation of Tc-MIBI on mitochrondrial membrane potential stands in contrast to unidirectional cellular influx of Tc-MIBI: estimates of unidirectional influx rates of Tc-MIBI were dominated by the plasma membrane potential. Use of the Goldman flux equation to analyze the $K_o$-dependence of influx in control buffer resulted in overestimation of an ideal Nernstian slope. From the perspective of quantitatively evaluating Tc-MIBI as a probe of plasma membrane potential, the valinomycin sensitivity of this overestimation indicated the small, but detectable, contribution of mitochondria to the control influx data. However, in the presence of valinomycin, Tc-MIBI demonstrated close to ideal Nernstian behavior.

Clinical Consequences

These data have implications for the initial biodistribution in vivo of intravenous bolus injections of Tc-MIBI. Initial tissue uptake in vivo, simulated in part by the unidirectional influx experiments in vitro, may be relatively more influenced by plasma membrane potentials compared to mitochondrial potentials. Therefore, Tc-MIBI, although a flow tracer, may also be a viability agent responsive to tissue energetics reflected in the plasma membrane potentials.

Having now generally described this invention, it will become readily apparent to those skilled in the art that many changes and modifications can be made thereto without affecting the spirit or scope thereof.

What is new and claimed and intended to be covered by Letters Patent of the United States is:

1. A method for enhancing the in vivo intracellular accumulation of a lipophilic cationic organometallic complex comprising coadministering to a cell said complex and an agent which decreases the intramembrane potential of said cell.

2. The method of claim 1 wherein the metal in said organometallic complex is selected from the group consisting of technetium and rhenium.

3. The method of claim 1 wherein said agent is a lipophilic anion.

4. The method of claim 3 wherein said anion is selected from the group consisting of tetraphenylborate and 8-anilino-1-naphthalene sulfonate ion.

5. The method of claim 1 wherein said agent is a dipolar compound.

6. The method of claim 5 wherein said dipolar compound is phloretin.

7. A diagnostic method comprising coadministering to an animal a lipophilic cationic organometallic complex in labelled form and an agent which decreases the intramembrane potential of cells in said animal, and detecting said label.

8. The method of claim 7 wherein the metal in said organometallic complex is selected from the group consisting of technetium and rhenium.

9. A method of in vivo cell imaging comprising coadministering a lipophilic cationic organometallic complex in labelled form and an agent which decreases the intramembrane potential of said cell and detecting said label.

10. The method of claim 1 wherein the metal in said organometallic complex is selected from the group consisting of technetium and rhenium.

11. A method of in vivo tissue imaging comprising coadministering to a subject a lipophilic cationic organometallic complex in labelled form and an agent which decreases the intramembrane potential of cells comprising said tissue and detecting said label.

12. The method of claim 11 wherein the metal in said organometallic complex is selected from the group consisting of technetium and rhenium.

13. The method of any one of claims 7, 9 or 11 wherein said agent is a lipophilic anion.

14. The method of claim 13 wherein said lipophilic anion is selected from the group consisting of 8-anilino-1 naphthalene sulfonate ion and tetraphenylborate anion.

15. The method of any one of claims 7, 9 or 11 wherein said agent is a dipolar compound.

16. The method of claim 15 wherein said compound is phloretin.

* * * * *

UNITED STATES PATENT AND TRADEMARK OFFICE
CERTIFICATE OF CORRECTION

PATENT NO. : 5,277,897
DATED : January 11, 1994
INVENTOR(S) : David R. Piwnica-Worms et al.

It is certified that error appears in the above-identified patent and that said Letters Patent is hereby corrected as shown below:

| Column | Line | |
|--------|------|--|
| 18 | 26 | "The method of claim 1" should read --The method of claim 9--. |

Signed and Sealed this

Fourteenth Day of June, 1994

Attest:

BRUCE LEHMAN

*Attesting Officer*   *Commissioner of Patents and Trademarks*